United States Patent [19]
McKee, Jr. et al.

[11] Patent Number: 5,311,568
[45] Date of Patent: May 10, 1994

[54] OPTICAL ALIGNMENT MEANS UTILIZING INVERSE PROJECTION OF A TEST PATTERN/TARGET

[75] Inventors: William J. McKee, Jr., Palo Alto; John R. Haire, San Jose, both of Calif.

[73] Assignee: Picker International, Inc., Cleveland, Ohio

[21] Appl. No.: 72,902

[22] Filed: Aug. 2, 1993

Related U.S. Application Data

[63] Continuation-in-part of Ser. No. 877,474, May 1, 1992, Pat. No. 5,218,626.

[51] Int. Cl.⁵ .................................... H05G 1/64
[52] U.S. Cl. .......................... 378/205; 378/206; 378/19; 250/214 VT
[58] Field of Search ............... 378/99, 116, 190, 205, 378/206, 210, 42, 62, 204, 19; 250/214 VT

[56] References Cited

U.S. PATENT DOCUMENTS

| | | | |
|---|---|---|---|
| 5,029,338 | 7/1991 | Aichinger et al. | 378/99 |
| 5,194,726 | 3/1993 | Jonkman | 378/99 |
| 5,218,626 | 6/1993 | McKee | 378/99 |

*Primary Examiner*—David P. Porta
*Assistant Examiner*—Don Wong
*Attorney, Agent, or Firm*—R. A. Notzen

[57] ABSTRACT

An imaging system comprised of a source of penetrative radiation 14, an image intensifier tube 18 and a video camera 38 is provided. The intensifier tube is comprised of a input screen 22 and an output screen 24. The intensifier tube converts radiation 20 impinging on the input screen into a visible light image 36 on the output screen 24. The video camera is operatively positioned to view the output screen of the intensifier. A light sampler 50 is operatively disposed in the visible light path between the image intensifier output screen 24 and the video camera input 38. The light sampler is comprised of a mirror 52, a focusing lens 54, a beam splitter 56, an aperture 58, a light source 78, a photo receptor 60 and an optical aligner 64. The optical aligner fixes the first mirror 52, the focusing lens 54, the half-mirror 56, the aperture 58, the light source 62 and the photo receptor 60 in optical alignment such that light originating on the output screen and received by the mirror 52 is directed to focusing lens 54 and to beam splitter 56. A portion of the light striking beam splitter 56 is reflected thereby and passes through aperture 58 and strikes photo receptor 60. Light originating from the light source 62 is directed to half-mirror 56 and passes therethrough to lens 54, to mirror 52 and to the output screen 22.

22 Claims, 4 Drawing Sheets

OPTICAL ALIGNMENT MEANS UTILIZING INVERSE PROJECTION OF A TEST PATTERN/TARGET

This application is a continuation-in-part of copending U.S. patent application Ser. No. 07/877,474 filed on May 1, 1992 to be issued as U.S. Pat. No. 5,218,626 on Jun. 8, 1993.

BACKGROUND OF THE INVENTION

The present invention relates to monitoring of x-ray exposures in imaging or inspection. It finds application in conjunction with diagnostic imaging apparatus, such as fluoroscopic imaging systems, and will be described with particular reference thereto. However, it should be appreciated that the invention will also find application in conjunction with other equipment where precise adjustable positioning of a radiation or visible light detection means is desirable.

Fluoroscopic imaging systems include a continuous or rapidly pulsed source of radiographic energy, such as that from an x-ray tube. The x-ray tube, when activated, propagates radiation through an object to be imaged, such as a human patient, onto a screen of fluorescent material. The object to be imaged is disposed in a gap between the x-ray source and the fluorescent screen.

X-ray radiation passing through the imaged object is attenuated according to the density of the material through which it has passed. Radiation passing through dense material, such as bone, will be attenuated more than radiation of similar energy passing through less dense materials, such as tissue. For uniformly intense radiation entering an object the radiation energy exiting the object is representative of the attenuation occurring within the object. Attenuated radiation impinging on the fluorescent screen is absorbed by fluorescent material thereon and converted into visible light image proportional to the radiation energy impinging at each point thereon. This conversion results in a two dimensional light image of the object represented by a plurality of different intensities of visible light. This light image can be visualized by the human eye or captured onto photographic film, which is generally more sensitive to light than to x-ray. The brightness of the fluorescent screen is sufficient to expose film placed in direct contact with the screen, but the light output is generally too low for direct diagnostic visualization, photographing with a camera, or viewing with a television camera. In many applications, a device is needed that will convert the x-rays into light and intensify, or increase, the brightness of the light. An image intensifier is such a device.

An image intensifier can be described as an evacuated glass bottle having a large bottom area as the input screen, and a small 'cap' area as the output screen. The x-ray source side of the input screen has a fluorescent material disposed thereon for absorbing the incident x-rays and converting a portion thereof into a low level visible light image. The low level visible light is absorbed by at photo cathode layer disposed in the evacuated bottle. The absorption of light by the photo cathode layer results in the emission of low energy electrons into the evacuated bottle. An electrical energy source applies a bias voltage between the photo cathode and the output screen which accelerates the low energy electrons in the tube towards the output screen. A plurality of electrodes in the intensifier tube form an electrostatic lens which provides controlled acceleration and convergence of the electrons into a smaller image area on the output screen. The accelerated electrons, which are now at a high kinetic energy potential, converge on and strike the output screen which has a phosphor thereon. The convergence of the electrons on the output screen phosphor results in scintillations of light corresponding in intensity to the kinetic energy of the electron striking at each point on the output screen. The sum of the individual scintillations of light on the output screen results in an image on the output screen that is representative of the radiation at the input of the intensifier tube.

The input end of a viewing means, such as a video camera, is held in fixed relation to the output of the intensifier tube in order that the output image of the intensifier tube can be viewed by the camera input. The video camera is part of a closed circuit television system which provides a visual image on an image monitor that is representative of the radiation image detected at the input of the intensifier.

In fluoroscopy, the patient is exposed to a low intensity source of continuous or rapidly pulsed x-ray radiation so that the radiologist can dynamically view the operation of the internal body structure being imaged on the image monitor. In practice a balance is made between minimizing patient exposure to x-ray radiation and the need to provide sufficient radiation to produce a quality diagnostic image. Factors that influence the amount of radiation delivered to a patient in a particular imaging sequence are the path length the radiation will traverse within the patient and the attenuation of the radiation within patient structures being imaged. Preliminary selection of x-ray dose rate can be made on the basis of empirical data however, because path length and attenuation are patient dependent variables, the actual effect of x-ray dose selection is not known until the output image is viewed.

In some fluoroscopic imaging systems the x-ray source, image intensifier, video camera and related components are contained within a movable gantry structure which allows the fluoroscopic system to be dynamically positioned about the patient. Moreover, the patient couch can be moved, relative to the x-ray source and image intensifier, during imaging operations to optimize the image view. Adjustment of the gantry and/or patient couch during imaging results in a change in the image intensity change due to fluctuations in the radiation path length or different radiation attenuation characteristics in different portions of the patient. Because the viewed image is capable of dynamically changing it is desirable to provide a means to dynamically adjust the x-ray dose rate to maintain the same image quality regardless of changing conditions.

One way to assure consistent image quality is to measure the x-ray dose rate after the x-rays have passed through the object to be imaged. A way to accomplish this is to measure the intensity of the light image on the output screen of the image intensifier. Accordingly, a light sampling means is disposed to view the output screen of the image intensifier. One such sampling means is comprised of a pair of mirrors or prisms disposed on an adjustable mirror assembly, an opaque housing with a light input hole in the side thereof and a photo multiplier tube (PMT) disposed in the housing. The PMT is an externally biased vacuum tube device that produces an electrical output in response to light input on a collector array therein. The PMT is disposed in the housing such that light passing through the light input hole strikes the collector array. In operation a first support arm operatively positions one of the mirrors into the visible light path and a second support arm supports the other mirror. The support arms hold the mirrors such that they are aligned to reflect light propagating from the intensifier output screen into the light input hole wherein the PMT collector converts the incident light into an electrical signal equivalent of the light received thereby. The output of the PMT is connected to a controller which adjusts the source of radiation such that the light image on the output screen is maintained at a predetermined brightness level for diagnostic viewing.

In application, the radiation passing through the object to be imaged passes through more areas of the object in the area of interest. These other areas routinely attenuate the radiation differently than the area of interest thereby resulting in different levels of brightness on the output screen. Accordingly, it is desirable to have the sampling means sample the light from a select area of the output screen corresponding to the area of interest in the imaged object. Adjustment of the above described sampling means requires the operator to insert an x-ray mask in the radiation beam path between the radiation source and the intensifier input screen. The mask is a sheet of x-ray opaque and x-ray transmissive pattern portions which causes a known x-ray pattern to be disposed on the input screen when the x-ray source is engaged. The x-ray pattern striking the input screen results in a representative light pattern on the output screen of the intensifier tube. To adjust the sampling means such that it monitors the light from a select portion of the intensifier output screen, it is necessary to engage the x-ray source with the x-ray mask in position. With the known pattern on the output screen the position of the mirror(s) is manually adjusted until the PMT receives light from the select portion of the output screen pattern. Thereafter, the x-ray source is disengaged and the x-ray mask is removed from the beam path.

One problem with the prior art devices is that the x-ray source must be engaged in order to adjust the viewing positions of the mirror(s) to a select portion of the image intensifier output screen.

The present invention contemplates a new and improved photo detection means which utilizes inverse projection of a test pattern to adjust the optical alignment of the detection means thereby avoiding the need to engage the radiation source during alignment.

SUMMARY OF THE INVENTION

In accordance with one aspect of the present invention an imaging system wherein a source of penetrative radiation directs a beam of penetrative radiation through an object to be imaged and onto the input screen of an image intensifier tube is provided. The image intensifier tube converts the radiation on the input screen into a visible light image on an output screen thereof. A viewing means views the output screen of the intensifier tube and transfers an electrical signal representative of the viewed image to a image monitor for display. A light sampling means comprised of a first light directing means, a light source, a light receiving means and an optical alignment means is positioned relative to the output screen such that the first light directing means views a portion of the output screen light propagating from the output screen. The alignment means positions the first light directing means and the light receiving means in alignment with the output screen along a first light path. The alignment means also positions the first light directing means and the light source in alignment with the output screen along a second light path. The first and second light paths are at least partially coincident.

In accordance with another aspect of the invention a second light directing means is positioned along the coincident light path for diverting at least a portion of at least one of the first and second light paths.

In accordance with another aspect of the invention an adjustable aperture, such as an iris, is disposed between the first light directing means and the light receiving means for controlling the percentage of the output screen light portion received by the light receiving means. A focusing lens is disposed between the first light directing means and the aperture.

In accordance with another aspect of the invention the focal distance between (a) the focusing lens and the aperture, and (b) the focusing lens and the light source are substantially the same distance.

In accordance with another aspect of the invention a means for adjustably positioning the first light directing means to detect light propagating from a select one of a plurality of locations lying along a first, imaginary line across the face of the output screen is provided. The adjustment means also includes means for adjustably positioning the first light directing means along a second, imaginary line across the face of the output screen wherein the second and first lines are substantially perpendicular.

In accordance with another aspect of the invention a means for sampling light propagating from an output screen of an image intensifier tube is provided. The sampling means includes a first light directing means disposed for intercepting light propagating from the output screen and for diverting a portion thereof along a path to a light receiving means. A light source is disposed for directing light at least partially along the path to the first light directing means. The first light directing means diverts the light source light to the output screen.

In accordance with another aspect of the invention a method of aligning a light sampling means to view light propagating from an image intensifier output screen of a diagnostic imaging system is provided. In the method, a sampling means light source is engaged. Light from the sampling means light source is directed to the output screen. The directed light is observed on the image monitor. The location of the directed light on the output screen is adjusted until the directed light is positioned at a desired location thereon.

An advantage of the invention is that a light source image is projected to a position on the output screen wherein the viewing means views the output screen and projects an image thereof to a image monitor thereby facilitating adjustment of the sampling means relative to the output surface without having to engage the radiation source.

Still other advantages will become apparent upon reading and understanding the following detailed description.

BRIEF DESCRIPTION OF THE DRAWINGS

The invention may take form in various parts, arrangements of parts or sizes of parts. The drawings are only for the purpose of illustrating the preferred embodiment and are not to be construed as limiting the invention.

DETAILED DESCRIPTION OF THE PREFERRED EMBODIMENT

Figure 1:
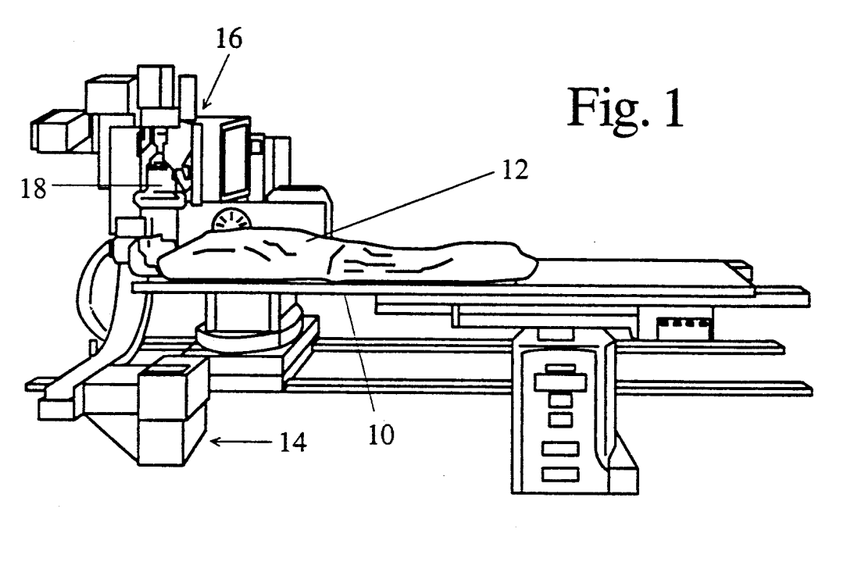
FIG. 1 is a perspective view of an exemplary x-ray system where the invention is used.

With reference to FIG. 1 in a fluoroscopic imaging system a generally x-ray transparent patient table 10 is selectively positioned to horizontally support a patient 12. The patient and table are disposed between an x-ray source 14 and an x-ray detection means 16. The x-ray source propagates x-radiation through the patient table and the patient. The x-rays passing through the patient are selectively attenuated by various anatomical structures within the patient. Upon exiting the patient the x-rays contain two dimensional radiographic information regarding the internal structure of the patient. The exiting x-rays are directed onto an x-ray detection means 16 which converts the radiographic image into a two dimensional light image.

Figure 2:
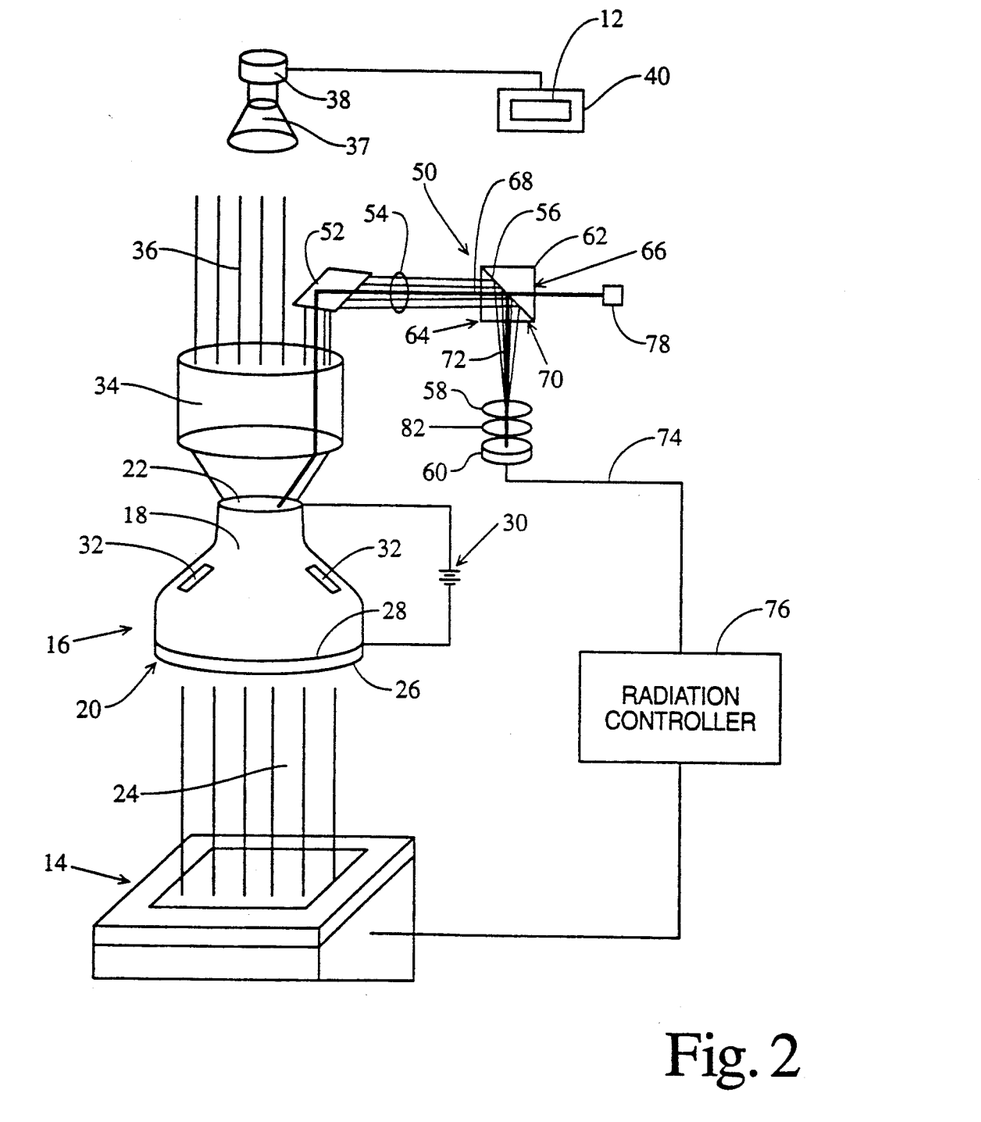
FIG. 2 is an exploded and isolated view of a light sampling means and associated intensifier tube and x-ray apparatus of the system of FIG. 1.

With reference to FIG. 2 and continuing reference to FIG. 1, the x-ray detection means 16 is comprised of an evacuated intensifier tube 18. The intensifier tube has a circular input screen 20 and a smaller circular output screen 22. The input screen 20 of the intensifier tube 18 includes a fluorescent screen 26 which converts the incident x-rays into a low brightness visible light proportional to the intensity of the x-rays impinging at each point thereon. A photo cathode 28 is disposed adjacent the fluorescent screen within the intensifier tube. Light from the fluorescent screen is absorbed by the photo cathode 28. The photo cathode releases a quantity of low energy electrons in proportion to the intensity of the visible light impinging at each point on the photo cathode. An electrical potential 30 is applied between the photo cathode 28 and the intensifier tube output screen 22. The electrical potential 30 accelerates the free electrons towards the output screen. A plurality of electrodes 32 in the intensifier tube form an electrostatic lens which provides controlled acceleration and convergence of the electrons into a smaller image area on the output screen 22. The accelerated electrons, which are now at a high kinetic energy potential, converge on and strike the output screen which has a phosphor thereon. A scintillating material disposed on the output screen absorbs the accelerated electrons and converts the electrons kinetic energy into visible light corresponding in intensity to the amount of kinetic energy in each electron striking the output screen. The resultant light pattern on the output screen is a viewable image of the radiographic image information present at the input to the image intensifier. A collimating objective 34 disposed adjacent the output screen 22 collimates and focuses the output image to infinity focus. The infinity focused light image 36 propagates through a television objective 37 and into a viewing means 38, such as a television camera. The viewing means 38 converts the light image into an electrical signal representation of the light image. The image monitor 40 converts the electrical signal into an image on the monitor for direct diagnostic viewing.

In the preferred embodiment, an optical sampling means 50 and the intensifier tube 18 are secured to a support means (not shown). The support means secures the sampling means 50 adjacent the intensifier tube such that the sampling means samples a portion of the light image 36 propagating from the output screen 22. The sampled light is used in a feedback mode to adjust the output of the x-ray source such that the intensity of light from the sampled position of the output screen 22 is maintained at a constant level. The sampling means 50 is comprised of a mirror 52, a focusing lens 54, a beam splitter 56 such as a half-mirror or prism, an aperture such as an adjustable iris 58, a photo sensor 60 such as a photo-multiplier tube, and an alignment means 62. The alignment means 62 defines a first end 64 and a second end 66 disposed on opposite ends thereof. The first and second ends, 64 and 66 respectively, define a first axis 68. The sampling means defines a third end 70 disposed between the first and second ends. The third end 70 is disposed substantially perpendicular to first axis 68 and defines second axis 72. The mirror 52 is positioned adjacent the first end 64 of the sampling means at an angle selected to detect light propagating from the intensifier output screen 22 and reflect the detected light along first axis 68. The focusing lens 54 is disposed between the first end 64 and the second end 66 for focusing light passing therethrough to a predetermined focal length. The beam splitter 56, is disposed between the focusing lens 54 and second end 66 along first axis 68 and adjacent second axis 72. The beam splitter reflects a portion of the light propagating from mirror 52 along second axis 72. Photo sensor 60 is disposed adjacent the third end 72 for viewing light propagating from beam splitter 56 along second axis 72. Iris 58 is disposed between the third end 70 and the photo sensor 60. In the preferred embodiment, the face of iris 58 is disposed at the focal plane of the focusing lens 54. Accordingly, the image at the focal plane is similar to the image on the output screen 22 other than the size and intensity. Second axis 72 passes through the central portion of iris 58. In the preferred embodiment, the iris aperture opening is variable from ten percent (10%) to eighty percent (80%) of its maximum aperture size thereby allowing a like percentage of the image present at the face of iris 58 to pass therethrough however, this is not to be construed as limitation of the invention. A light image traveling from the output screen 22 and reflected by mirror 52 passes thorough lens 54 and is partially reflected by beam splitter 56. A percentage of the partially reflected light image passes through iris 58 and strikes photo sensor 60. The mirror 52 and the photo sensor 60 are in alignment with the output screen along a first light path. The photo sensor output 74 is connected to a radiation controller 76 for adjusting the output of the radiation source 14 in response to the output of the photo sensor thereby maintaining the amount of light present at the output screen 24 of the image intensifier at a substantially constant level regardless of the radiation attenuation occurring in the object under examination. The elements of the preferred embodiment described up to this point are used to view a portion of the image created on the output screen 22 and adjust the x-ray source accordingly.

A light source 78 is positioned adjacent the second end 66. Light from light source 78 partially passes through beam splitter 56 and strikes lens 54. The light propagating through lens 54 strikes mirror 52 and is reflected thereby through the collimating objective 34 to the output screen 22. The light source 78 and the mirror 52 are in alignment with the output screen along a second light path. The light from the light source striking the output screen 22 is used to align the sampling means to the output screen. Alternatively, a pattern, such as a cross-hair, is introduced into the light source path so that a corresponding pattern appears on the output screen as an alignment target. In the preferred embodiment the light source/pattern 78 is disposed at the focal plane of the focusing lens 54. The size of the light source light or pattern striking the output screen is a function of the diameter of the light source times the collimator 34 focal length over the focusing lens 54 focal length. For example, if the diameter of the light source 78 is 1 mm, and the focal length of the collimator 34 is 122 mm and the focal length of focusing lens 54 is 40 mm the diameter of the light source light on the output screen will be about 3.05 mm. It should be appreciated, however, this is not to be construed as a limitation of the invention.

It should be appreciated that at least a portion of the first and second light paths are substantially coincident along the path between the mirror 52 and the beam splitter 56.

In the above described embodiment the focal length between the focusing lens 54 and the light source 78 and the focusing lens 54 and iris 58 are approximately the same distance. However, it is to be appreciated that this is not to be construed as a limitation of the present invention.

Moreover, it should be appreciated that the focusing lens 54 and/or the iris 58 could be eliminated from the preferred embodiment without affecting the fundamental operation of the sampling means. However, the focusing lens 54 and iris 58 enhance the effectiveness of the above described sampling means.

The beam splitter 56 is constructed such that light impinging thereon from either direction partially passes therethrough and is partially reflected thereby. Accordingly, it should be appreciated that the iris 58 and the photo receptor 60 can be located adjacent the second end 66 and light source 86 can be located in the third end 72 without affecting the operation of the sampling means 50.

In operation once the iris opening has been established further adjustment of the iris is not required. Accordingly, an iris having a fixed aperture size can also be used.

Figure 3:
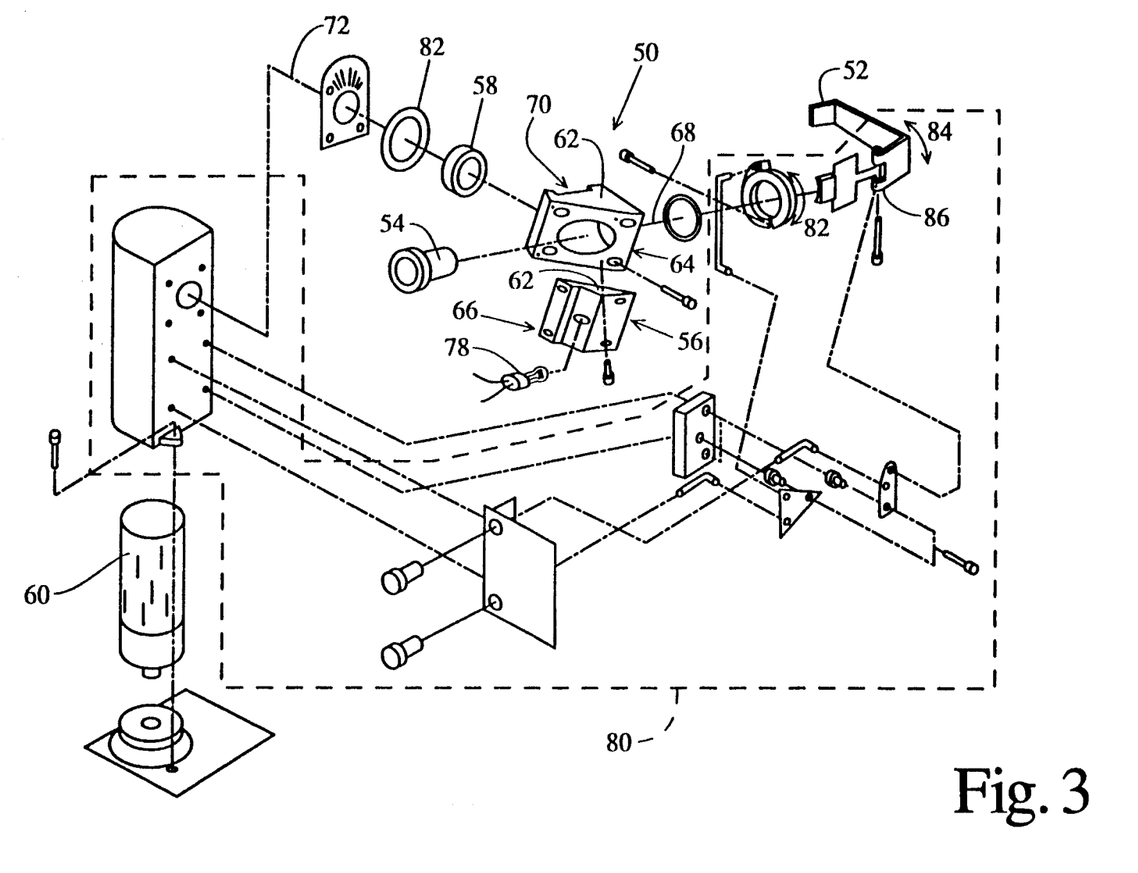
FIG. 3 is an exploded isolated view of the light sampling means of FIG. 2 and corresponding adjustment assembly.

With reference to FIG. 3, and continuing reference to FIGS. 1 and 2, the sampling means 50 is secured to an adjustment assembly 80. The adjustment assembly 80 provides for rotational motion 82 of the mirror 52 around first axis 68 and pivotal motion 84 of the mirror 52 about pivot axis 86 through an assembly of levers and arms. In the embodiment illustrated in FIG. 3, first axis 68, pivot axis 86 and the direction of light propagating from the output screen 22 are generally orthogonal to each other. The adjustment assembly 80 provides progressive adjustment of the aim of mirror 52 relative to the output screen 22 by rotating the sampling means around first axis 68 and/or pivoting the sampling means about pivot axis 86. It should be appreciated that other adjustment assemblies that allow for progressive adjustment of the alignment means relative to the output screen are also contemplated. One such adjustment assembly is illustrated in copending U.S. patent application Ser. No. 07/877,474, of William J. McKee, to be issued as U.S. Pat. No. 5,218,626 on Jun. 8, 1993 which is expressly incorporated herein by reference.

To align the sampling means 50 the light source 78, the television camera 38 and the image monitor 40 are engaged. Light from the light source 78 partially passes through beam splitter 56 to focusing lens 54. The light passing through the focusing lens 54 is reflected by the mirror 52 towards the collimating objective 34. The light propagating from mirror 52 passes through the collimating objective 34 and strikes the output screen 22. While viewing the output screen 22 on the image monitor 40, the adjustment assembly 80 is rotatably adjusted 82 about first axis 68 and/or pivotally adjusted 84 about axis 86 to direct light source light to a select one of a plurality of locations lying across a first and second imaginary line respectively across the face of the output screen until the light appearing on the output screen is at a desired location thereon. The first and second imaginary lines are substantially perpendicular. It should be appreciated that alignment of the light source light to the output screen 22 results in adjustment of the part of the output screen image that is presented to the iris aperture during imaging operation. Once the sampling means is aligned the light source is disengaged.

Once aligned the imaging system is prepared for use. The object to be imaged 12 is disposed between the x-ray source 14 and the image intensifier input screen 20. The x-ray source is engaged thereby resulting in a light output on the intensifier output screen 22. The light output propagates from the output screen 22 and passes through collimating objective 34. A portion of the output screen light passing through the collimating objective 34 is intercepted by the mirror 52 and reflected through the focusing lens 54 along first axis 68. The reflected light strikes the beam splitter 56 which partially reflects the output screen light along axis 70. The partially reflected light passes through iris 58 and strikes photo sensor 60. Light reaching the photo sensor causes the photo sensor to create a output signal corresponding to the intensity of light received thereby. The photo sensor output 74 is connected to the radiation controller 76. The radiation controller 76 adjusts the output of the radiation source 14 in response to the photo sensor output 74 such that the output screen image is maintained at a constant light intensity during the procedure.

Figure 4:
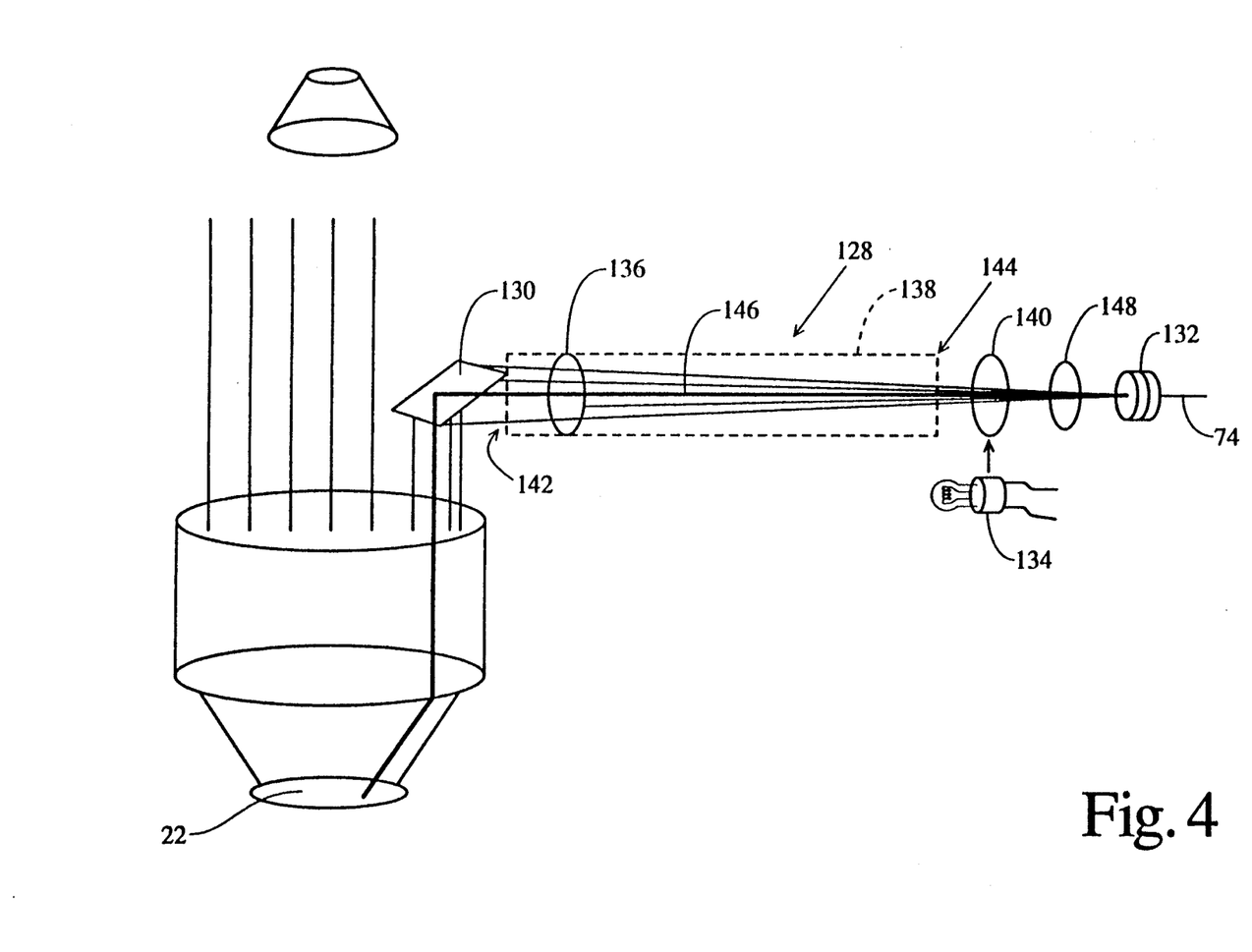
FIG. 4 is an isolated view of a light sampling means according to an alternate embodiment of the invention relative to the output screen of an image intensifier.

With reference to FIG. 4 and continuing reference to all previous Figures, in an alternate embodiment of the invention, the optical sampling 128 means is comprised of a mirror 130, a photo sensor 132, a light source 134, a focusing lens 136, an alignment means 138 and an iris 140. The alignment means 138 has a first end 142 and a second end 144 disposed on opposite ends along longitudinal axis 146. An adjustment assembly 80 of the type described in conjunction with FIG. 3 adjustably secures the alignment means 128 such that longitudinal axis 146 is generally perpendicular to the direction of light propagating from the face of the output screen 22. The mirror 130 is secured adjacent the first end 142 at an angle selected to detect light originating from the intensifier output screen 22 and reflect said detected light along axis 146. In operation, the photo sensor 132 is disposed adjacent the second end 144, for receiving light propagating from the first mirror 130 along axis 146. The iris 140 is disposed between the second end 144 and the photo sensor 132. The iris 140 is also disposed at the focal plane of the focusing lens 136.

To align the sampling means the radiation source is disengaged and the light source 134 replaces iris 140 along axis 146. The light source 134, the television camera 38 and the image monitor 40 are engaged. Light from the light source 134 propagates along axis 146, through lens 136 and strikes mirror 130. Mirror 130 reflects the light to the intensifier output screen 22. While viewing the output screen 22 on the image monitor, the adjustment assembly 80 is adjusted. Once the reflected light is at the desired position on the output screen 22, the light source is disengaged and removed from adjacent the second end 144 of the alignment means 128 and the iris 140 is moved back into position.

In operation, the object to be imaged 12 is disposed between the x-ray source 14 and the image intensifier input screen 20. The x-ray source is engaged thereby resulting in a light output on the intensifier output screen 22. A portion of the light from the output screen 22 is reflected by mirror 130 along axis 146. The reflected light passes through lens 136. The iris 140 is disposed at the focal plane of the lens 136. Thus, the image at the focusing lens focal plane is similar to the image on the output screen 22 other than the size and intensity. Accordingly, adjusting the size of the aperture opening of iris 140 determines the percentage of the image utilized by the photo sensor 132 to monitor the image brightness. The light reaching the photo sensor 132 causes the photo sensor to create a signal corresponding to the amount of light received thereby. The photo sensor output 74 is connected to the radiation controller 76 which adjusts the output of the radiation source to maintain the viewed the output screen 22 at a constant light intensity.

Photo sensors, such as a PMT, have a limited range of input over which the sensor can operate linearly. For the present invention, if the brightness of the light received by the photo sensor is greater than the capacity of the photo sensor to accept, the photo sensor output does not vary in accordance with the input light. Accordingly, the ability of the radiation controller is affected and the output image light is not properly adjusted to maintain the image at a select brightness level. The operating range, or gain, of the photo sensor can be extended by introducing a neutral density (ND) filter (82, 148) into the light path between the beam splitter and the photo sensor. ND filters attenuate light across all spectra of light equally. Accordingly, as the output screen light becomes brighter ND filters having select attenuations are introduced into the light path to maintain the photo sensor in its ideal detection range.

The above invention has been described with reference to the preferred embodiment. Obvious modifications and combinations will occur to others upon reading and understanding the preceding description. It is intended that the invention be construed as including afl such modifications, combinations and alterations insofar as they come within the scope of the appended claims or the equivalents hereof.

Having described the preferred embodiment the invention now claimed to be:

1. A diagnostic imaging system including:
   a source of penetrative radiation;
   an image intensifier tube having an input screen and an output screen, the input screen disposed to receive radiation from the source, the source and input screen defining a gap therebetween for receiving an object under examination, the output screen producing a visible light image on a face thereof corresponding to radiation received by the input screen;
   a viewing means for viewing the visible light image and converting the light image into a video signal for displaying on an image monitor; and
   a light sampling means positioned relative to the output screen for sampling a portion of the output screen light, said light sampling means comprised of,
   a first light directing means;
   a light receiving means;
   a light source; and
   an alignment means for positioning the first light directing means and the light receiving means in alignment with the output screen along a first light path and for positioning the first light directing means and the light source in alignment with the output screen along a second light path, said first and second light paths at least partially coincident.

2. The imaging system as set forth in claim 1 further including a second light directing means positioned along the coincident light paths for diverting at least a portion of at least one of said first and second light paths.

3. The imaging system as set forth in claim 1 further including an aperture disposed between the first light directing means and the light receiving means for controlling the percentage of the output screen light portion received by the light receiving means.

4. The imaging system as set forth in claim 3 further including a focusing lens disposed between the first light directing means and the aperture.

5. The imaging system as set forth in claim 4 wherein the focal distances between (a) the focusing lens and the aperture, and (b) the focusing lens and the light source are substantially the same.

6. The imaging system as set forth in claim 1 further including an adjustment means for adjustably aligning the light sampling means to a select portion of the output screen.

7. The imaging system as set forth in claim 6 wherein the adjustment means further includes means for adjustably positioning the first light directing means to detect light propagating from a select one of a plurality of locations lying along a first, imaginary line across the face of the output screen.

8. The adjustment means as set forth in claim 7 wherein the adjustment means further includes means to detect light propagating from a select one a plurality of locations lying along a second, imaginary line across the face of the output screen, said second line substantially perpendicular to said first line.

9. The imaging system as set forth in claim 2 wherein the second light directing means is a beam splitter wherein light incident thereon partially passes therethrough and is partially reflected thereby.

10. A means for sampling light propagating from an output screen of an image intensifier tube, said means comprising: a light receiving means;
   a first light directing means disposed for reflecting light propagating from the output screen along a path to said light receiving means; and
   a light source disposed for directing light at least partially along the path to the first light directing means, the first light directing means diverting said light source light to the output screen.

11. The sampling means as set forth in claim 10 further including a second light directing means disposed along the path for reflecting a portion of the diverted output screen light to the light receiving means, said second light directing means allowing a portion of said light source light to pass therethrough and propagate along the path to the first light directing means.

12. The sampling means as set forth in claim 10 further including a second light directing means disposed along the path, said second light directing means allowing a portion of the diverted output screen light to pass therethrough and strike the light receiving means, said second light directing means disposed to receive light from the light source and direct said light source light along the path to the first light directing means.

13. The sampling means as set forth in claim 11 further including an aperture disposed adjacent the light receiving means for controlling the percentage of the output screen light portion received by the light receiving means.

14. The sampling means as set forth in claim 13 further including a focusing lens disposed between the first and second light directing means along the path.

15. The sampling means as set forth in claim 14 wherein the focal distances between (a) the focusing lens and the aperture and (b) the focusing lens and the light source are substantially the same.

16. The sampling means as set forth in claim 10 further including an adjustment means for adjustably aligning the light sampling means to a select portion of the output screen.

17. The sampling means as set forth in claim 16 wherein the adjustment means further includes means for pivotally adjusting the first light directing means to detect light propagating from a select one of a plurality of locations lying along a first, imaginary line across the face of the output screen.

18. The sampling as set forth in claim 17 wherein the adjustment means further includes means for rotatably adjusting the first light detecting means to detect light propagating from a select one a plurality of locations lying along a second, imaginary line across the face of the output screen, said second line substantially perpendicular to said first line.

19. The sampling means as set forth in claim 11 wherein the second light directing means is a beam splitter wherein a portion of the light incident thereon passes through unreflected and another portion of the light incident thereon is reflected thereby.

20. A method of aligning a light sampling means to view a light image propagating from an image intensifier output screen of a diagnostic imaging system, the method comprising the steps of:
engaging a light source,
directing light from the light source to the output screen;
observing the light falling on the output screen; and
adjusting the location of the directed light on the output screen until the directed light is positioned at a desired location thereon with respect to the light sampling means.

21. The method as set forth in claim 20 wherein the adjusting step includes at least one of the steps of:
rotating the sampling means on an adjustment assembly about a first axis generally perpendicular to the direction of light propagating from the output screen; and
pivoting the light sampling means on the adjustment assembly about a second axis generally perpendicular to the first axis, said first axis, said second axis and the direction of light propagating from the output screen generally orthogonal to each other.

22. The method as set forth in claim 20 wherein the observing step includes at least one of the steps of:
engaging a viewing means for viewing the output screen and converting the viewed image into an electrical signal representative thereof; and
engaging a image monitor for converting the electrical signal into an image.

* * * * *